United States Patent
Fan et al.

(10) Patent No.: US 11,746,033 B2
(45) Date of Patent: Sep. 5, 2023

(54) METHOD FOR TREATING PRODUCTION WASTEWATER FROM THE PREPARATION OF PROPYLENE OXIDE BY CO-OXIDATION

(71) Applicant: Wanhua Chemical Group Co., Ltd., Shandong (CN)

(72) Inventors: Zhenlong Fan, Shandong (CN); Yanfeng Dong, Shandong (CN); Fanxue Zeng, Shandong (CN); Jianchu Ye, Shandong (CN); Bingwen Leng, Shandong (CN); Genhai Yu, Shandong (CN); Xinchun He, Shandong (CN); Hongke Zhang, Shandong (CN)

(73) Assignee: Wanhua Chemical Group Co., Ltd., Shandong (CN)

( * ) Notice: Subject to any disclaimer, the term of this patent is extended or adjusted under 35 U.S.C. 154(b) by 0 days.

(21) Appl. No.: 17/291,573

(22) PCT Filed: Dec. 19, 2019

(86) PCT No.: PCT/CN2019/126780
§ 371 (c)(1),
(2) Date: May 5, 2021

(87) PCT Pub. No.: WO2021/120133
PCT Pub. Date: Jun. 24, 2021

(65) Prior Publication Data
US 2022/0306506 A1    Sep. 29, 2022

(51) Int. Cl.
*C02F 9/00*    (2023.01)
*B01D 1/26*    (2006.01)
(Continued)

(52) U.S. Cl.
CPC .................. *C02F 9/00* (2013.01); *B01D 1/26* (2013.01); *B01D 17/0208* (2013.01);
(Continued)

(58) Field of Classification Search
CPC .. C02F 9/00; C02F 1/001; C02F 1/043; C02F 1/048; C02F 1/40; C02F 1/66;
(Continued)

(56) References Cited

U.S. PATENT DOCUMENTS 3,881,996 A    5/1975    Schmidt
5,993,673 A    11/1999   Evans et al.

FOREIGN PATENT DOCUMENTS

CN    102093316 A    6/2011
CN    104230684 A    12/2014
(Continued)

OTHER PUBLICATIONS

English language machine translation of CN102093316A, 8 pages, No Date.*
(Continued)

*Primary Examiner* — Pranav N Patel
(74) *Attorney, Agent, or Firm* — Norton Rose Fulbright US LLP; James R. Crawford (57) ABSTRACT

Method for treating production wastewater from the preparation of propylene oxide by co-oxidation. The wastewater includes a first portion of wastewater having a peroxide content of 2000 mg/L or more and a second portion of wastewater having a peroxide content of 50 mg/L or less.

11 Claims, 1 Drawing Sheet

(51) Int. Cl.
  *C02F 1/04*        (2023.01)
  *B01D 17/02*       (2006.01)
  *C02F 1/00*            (2023.01)
  *C02F 1/40*            (2023.01)
  *C02F 1/66*            (2023.01)
  *C02F 1/72*            (2023.01)
  *C02F 3/00*            (2023.01)
  *C02F 101/10*          (2006.01)
  *C02F 101/32*          (2006.01)
  *C02F 103/36*          (2006.01)

(52) U.S. Cl.
  CPC .............. *C02F 1/001* (2013.01); *C02F 1/043* (2013.01); *C02F 1/048* (2013.01); *C02F 1/40* (2013.01); *C02F 1/66* (2013.01); *C02F 1/725* (2013.01); *C02F 3/00* (2013.01); *C02F 2101/10* (2013.01); *C02F 2101/32* (2013.01); *C02F 2103/36* (2013.01); *C02F 2301/046* (2013.01)

(58) Field of Classification Search
  CPC ........ C02F 1/725; C02F 3/00; C02F 2101/10; C02F 2101/32; C02F 2103/36; C02F 2301/046; C02F 1/722; C02F 2301/043; C02F 2103/38; C02F 1/58; B01D 1/26; B01D 17/0208; B01D 3/143; B01D 17/02; B01D 35/02; C07D 301/19; C07C 29/132; C07C 29/80
  See application file for complete search history.

(56) References Cited

FOREIGN PATENT DOCUMENTS

| CN | 105272941 A | 1/2016 |
|---|---|---|
| CN | 106064864 A | 11/2016 |
| CN | 207016649 U | 2/2018 |
| CN | 107987038 A | 5/2018 |
| EP | 1096982 B1 | 1/2005 |

OTHER PUBLICATIONS

English language machine translation of CN105272941A, 6 pages, No Date.*
Office Action dated Jun. 14, 2022 by the CIPO in the corresponding Patent Application No. 201911320965.8, with English translation.
International Search Report in connection with PCT Appl. No. PCT/CN2019/126780.
European Search Report issued in corresponding patent application No. 19948206.8, dated Mar. 15, 2022.

* cited by examiner

METHOD FOR TREATING PRODUCTION WASTEWATER FROM THE PREPARATION OF PROPYLENE OXIDE BY CO-OXIDATION

CROSS REFERENCE TO RELATED APPLICATIONS

The present application is a national phase application under 35 U.S.C. § 371 of International Application No. PCT/CN2019/126780 filed Dec. 19, 2019, the entire contents of which are incorporated herein by reference in their entirety.

TECHNICAL FIELD

The present disclosure belongs to the field of wastewater treatment and in particular, relates to a method for treating production wastewater from the preparation of propylene oxide by co-oxidation.

BACKGROUND

Propylene oxide (PO) is a colorless, transparent and flammable liquid with a low boiling point. PO, as the third type of propylene derivatives following acrylonitrile and polypropylene, plays an important role in the production of organic chemicals. At present, the main methods for producing propylene oxide in China include chlorohydrination, co-oxidation (including the co-oxidation thiobarbituric acid method for co-production of methyl tert-butyl ether, that is, the POMTBE method, the ethylbenzene co-oxidation method for co-production of styrene, that is, the POSM method, and the cumene peroxide method, that is, the POCHP method), and direct oxidation (including the HPPO method with hydrogen peroxide as an oxidizing agent).

With the increasingly stringent requirements of energy conservation, environmental protection and low carbon production in China, conventional chlorohydrination method has been increasingly restricted in enterprise production and development space because this method may cause serious pollution. Although the HPPO method has the advantages of mild reaction conditions and no pollution, its cost is high due to the utilization of catalyst and hydrogen peroxide. Some of processes of the co-oxidation method involve the co-production of isobutane or ethylbenzene and thus are suitable for large plant production. In conclusion, the processes POSM and POCHP of the co-oxidation method have more development value.

The wastewater produced by the processes for producing the PO by co-oxidation, represented by POSM and POCHP, is characterized by large water consumption, high contents of salts and organics, etc. At the same time, part of the stream wastewater contains peroxides which are very easy to self-decompose, resulting in high safety risk. The methods used in industry to treat the above-mentioned wastewater are generally the sodium thiosulfate reduction process, the alkali addition decomposition process, the fluidized bed catalytic decomposition process, and the fluidized bed enzymatic decomposition process. After the peroxide is removed, the wastewater is mixed with other wastewater in the device and then subjected to incineration treatment. However, the above methods have disadvantages such as low peroxide removal efficiency, long reaction time, high operation cost, and large oxygen generation amount, and it is difficult to improve the safety and stability of the process essentially. Meanwhile, the cost of the direct incineration treatment of the wastewater is high, and valuable components in the wastewater cannot be recovered, increasing the production unit consumption.

At present, there are few researches on POSM and POCHP wastewater treatment processes, and there is no relatively mature systematic process flow. Therefore, there is an urgent need to develop a treatment process suitable for treating wastewater which is high in salinity and organic matter content and contains peroxides.

SUMMARY

Therefore, the object of the present disclosure is to provide a method for treating production wastewater from the preparation of propylene oxide by co-oxidation. The treatment method is suitable for treating wastewater which is high in salinity and organic matter content and contains peroxides, and can remove the peroxides in the production wastewater from the preparation of propylene oxide by co-oxidation, improve the biodegradability of wastewater, and reduce the difficulty and cost of wastewater treatment.

To achieve the above object, the present disclosure adopts the following solutions:

A method for treating production wastewater from the preparation of propylene oxide by co-oxidation, where the production wastewater includes a first portion of wastewater having a peroxide content of 2000 mg/L or more and a second portion of wastewater having a peroxide content of 50 mg/L or less. The method includes the following steps:

(1) pre-subjecting the first portion of wastewater to a catalytic oxidation treatment to remove peroxides therefrom to obtain effluent wastewater;

(2) feeding mixed wastewater obtained by mixing at least portion of the effluent wastewater with the second portion of wastewater into a multi-effect evaporation unit for treatment, where the multi-effect evaporation unit includes:

a first rectifying column, configured to rectify the mixed wastewater to concentrate the mixed wastewater to obtain a first overhead material from the top of the first rectifying column and first concentrated wastewater from the bottom of the first rectifying column as a first column kettle liquid;

a second rectifying column, configured to rectify the first column kettle liquid from the first rectifying column to further concentrate the first column kettle liquid to obtain a second overhead material from the top of the second rectifying column and secondary concentrated wastewater from the bottom of the second rectifying column as a second column kettle liquid (that is, concentrated wastewater); and a third rectifying column, configured to rectify the first overhead material from the first rectifying column and the second overhead material from the second rectifying column for oil-water separation to obtain an oil phase from the top of the third rectifying column as a third overhead material (that is, light fraction-removal oil phase) and an aqueous phase from the bottom of the third rectifying column as a third column kettle liquid (that is, light fraction-removal column kettle wastewater);

(3) subjecting the second column kettle liquid to an incineration treatment to obtain a salt residue; and (4) subjecting the third column kettle liquid to a biochemical treatment to remove organic matters therefrom.

The co-oxidation process for the preparation of propylene oxide in the present disclosure includes the ethylbenzene co-oxidation method for co-production of styrene (that is, the POSM method) and the cumene peroxide method (that is, the POCHP method), which, as is appreciated by those skilled in the art, mainly includes a peroxidation unit, an epoxidation unit, a refining unit, and the like. The production wastewater from the preparation of propylene oxide by co-oxidation in the present disclosure refers to production wastewater from the preparation of propylene oxide by the prevailing co-oxidation method (including POSM method and POCHP method). For example, the aqueous phase condensed by the peroxide tail gas from the peroxide tail gas absorption tower/condensate tank and the peroxide alkaline-washing wastewater from the peroxide alkaline-washing settling tank are taken as the first portion of wastewater, and the ethylbenzene alkaline-washing wastewater, styrene alkaline-washing wastewater, vacuum system condensate, separated water from the propylene recovery system, and water-washing water phase from the PO refining system are taken as the second portion of wastewater. For the specific process of preparing propylene oxide by POSM, the reference may be made to "Technical Progress and Market Analysis of Propylene Oxide Production", whose classification No. F426.7, TQ223.26 and which is edited by Chen Lu from Shanghai Research Institute of Petrochemical Technology of China Petroleum and Chemical Corporation.

In the present disclosure, when the catalytic oxidation treatment of step (1) is carried out, the content of peroxide is calculated based on the content of hydrogen peroxide. Preferably, in the first portion of wastewater, the content of peroxide is 2000 mg/L to 28000 mg/L, preferably 3000 mg/L to 25000 mg/L. The COD is less than or equal to 100000 mg/L, and preferably the COD is less than or equal to 80000 mg/L. Preferably, the catalytic oxidation treatment is carried out in a catalytic oxidation reactor, and the useful catalytic oxidation reactor may be a fixed bed reactor.

When the material system in the catalytic oxidation reactor has a low pH and is acidic, it is not conducive to carrying out the catalytic oxidation reaction in the catalytic oxidation reactor. Therefore, in one embodiment, a portion of the effluent wastewater is cycled to an inlet of the catalytic oxidation reactor in a cycling ratio of 1 to 5. The cycling ratio refers to the ratio of the amount of effluent wastewater cycled to the catalytic oxidation reactor to the total amount of effluent wastewater. Preferably, an alkaline solution (for example, a NaOH solution) is added to the cycled portion of the effluent wastewater to increase the pH value of this portion of the effluent wastewater so that the alkaline solution is conveyed to the catalytic oxidation reactor along with this portion of the effluent wastewater to improve the pH of the material system in the catalytic oxidation reactor, promote the progress of the catalytic oxidation reaction, and improve the reaction efficiency of the catalytic oxidation reaction. Further preferably, the addition amount of the alkaline solution (for example, a NaOH solution) to the cycled portion of the effluent wastewater is the amount which can make the pH of the material system in the catalytic oxidation reactor rise to 6 to 13, preferably, 9 to 10, to further improve the reaction efficiency of the catalytic oxidation reaction. Further preferably, the concentration of the NaOH solution is 20 wt % to 40 wt %, such as 24 wt %, 28 wt %, 32 wt %, and 36 wt %. The operation of cycling a portion of the effluent wastewater, in one aspect, can dilute the concentration of hydrogen peroxide in the feed wastewater and improve the operational stability in the catalytic oxidation reactor, and in another aspect, the alkali addition to this cycled stream has a small influence on pH fluctuations in the catalytic decomposition reactor.

In one embodiment, the catalyst used for the catalytic oxidation treatment is a complex catalyst of $MnO_2$ and NiO, where the mass ratio of $MnO_2$ to NiO is (0.5 to 2):1, for example, 1:1, 1.2:1, and 1.5:1. The complex catalyst of $MnO_2$ and NiO may be obtained by mixing in the proportion and calcining manganese nitrate and nickel nitrate, where the calcination temperature is 500° C. to 600° C. and the calcination duration is 1.5 h to 2.5 h. Preferably, the catalytic oxidation treatment is carried out under the following catalytic oxidation conditions: a temperature of 20° C. to 80° C., preferably, 50° C. to 70° C., and a feed space velocity of 0.5 $h^{-1}$ to 4 $h^{-1}$, preferably, 1 $h^{-1}$ to 2 $h^{-1}$.

In the present disclosure, the first portion of wastewater is separately subjected to the catalytic oxidation treatment so that the peroxide in the first portion of wastewater rapidly generates a large amount of active oxygen radicals [O]. In this way, the organic matter which is difficult to be biochemically decomposed in the first portion of wastewater is catalytically decomposed into $CO_2$, $H_2O$, methanol, small-molecule carboxylic acid, and the like, and the peroxide in the first portion of wastewater is converted into a reaction raw material (for example, the peroxide ethylbenzene hydroperoxide (EBHP)/cumene hydrogen peroxide (CHP) are directionally converted into phenylethanol/dimethylbenzyl alcohol). Therefore, the biodegradability of the wastewater is improved while the concentration of the peroxide is reduced, and the difficulty and cost of the wastewater treatment are reduced. At the same time, it avoids the disadvantage that the amount of wastewater to be treated by the catalytic oxidation reactor is large when the first portion of wastewater and the second portion of wastewater are mixed and treated together, and the material processing capacity of the catalytic oxidation reactor is reduced. The content of peroxide in the effluent wastewater obtained after the catalytic oxidation treatment in step (1) is reduced to 50 mg/L to 1000 mg/L.

The peroxide ethylbenzene hydroperoxide (EBHP) is present in the production wastewater from the preparation of propylene oxide by the POSM process. Ethylbenzene is the raw material of the peroxidation unit in the POSM process. The phenylethanol converted from the peroxide EBHP is returned to the refining unit in the POSM process for refining and purification to obtain purified phenylethanol. The refined phenylethanol is fed to the phenylethanol dehydration reactor in the POSM process for dehydration treatment to obtain styrene which is produced as a by-product for storage, use or sale. Through the method of treating production wastewater from the preparation of propylene oxide by co-oxidation of the present disclosure, additional styrene can be recovered at a rate of 200 kg/h. If the system runs for 8000 h a year and the market unit price of styrene is 7400 RMB/ton, the economic benefit for a year may be 12.8 million RMB. Therefore, directional conversion of the peroxide ethylbenzene hydroperoxide (EBHP) into phenylethanol helps to reduce the capital consumption of the preparation of propylene oxide by the POSM process, which is equivalent to an indirect reduction of the unit consumption of ethylbenzene. The recovery rate of the peroxide EBHP may reach 80% (mole percent) or more and even 90% or more with small loss.

The peroxide cumene hydrogen peroxide (CHP) is present in the production wastewater from the preparation of propylene oxide by the POCHP process. Cumene is the raw material of the peroxidation unit in the POCHP process. The dimethylbenzyl alcohol converted from the peroxide CHP is returned to the refining unit in the POCHP process for refining, purification and hydrogenolysis to obtain cumene.

The cumene is fed to the peroxidation unit in the POCHP process as the raw material for reuse or as a by-product for storage, use or sale. Through the method of treating production wastewater from the preparation of propylene oxide by co-oxidation of the present disclosure, additional cumene can be recovered at a rate of 130 kg/h. If the system runs for 8000 h a year and the market unit price of cumene is 8000 RMB/ton, the economic benefit for a year may be 8.32 million RMB. Therefore, directional conversion of the cumene hydrogen peroxide (CHP) into dimethylbenzyl alcohol helps to reduce the capital consumption of the preparation of propylene oxide by the POCHP process, which is equivalent to an indirect reduction of the unit consumption of cumene. The recovery rate of the peroxide CHP may reach 80% (mole percent) or more and even 90% or more with small loss.

Therefore, the conversion of the peroxide in the first portion of wastewater into the reaction raw material (for example, the directional conversion of the peroxide ethylbenzene hydroperoxide (EBHP)/cumene hydrogen peroxide (CHP) into phenylethanol/dimethylbenzyl alcohol) helps to reduce the unit consumption of ethylbenzene/cumene in the preparation of propylene oxide by co-oxidation.

In the present disclosure, when the treatment of step (2) is carried out, the effluent wastewater is mixed with the second portion of wastewater to obtain mixed wastewater. For the mixed wastewater, the COD is less than or equal to 50,000 mg/L, preferably 10,000 mg/L to 30,000 mg/L, the pH value is 5 to 12, preferably 8 to 10, and the content of salts is 1 wt % to 20 wt %, preferably 5 wt % to 10 wt % (the salts here include sodium formate, sodium acetate and sodium benzoate, etc.).

In the multi-effect evaporation unit, the mixed wastewater is rectified by the first rectifying column, in which most of the water and a small part of organic matters rise to the top of the first rectifying column to form a first overhead material, and the remaining water and salts descend to the bottom of the first rectifying column to form a first column kettle liquid; the first column kettle liquid is rectified by the second rectifying column, in which most of the water and a small part of organic matters rise to the top of the second rectifying column to form a second overhead material, and the remaining water and salts descend to the bottom of the second rectifying column to form a second column kettle liquid; and the first overhead material from the first rectifying column and the second overhead material from the second rectifying column are rectified by the third rectifying column, in which most of the organic matters rise to the top of the third rectifying column to form a third overhead material (that is, light fraction-removal oil phase), and most of the water and a small part of organic matters descend to the bottom of the third rectifying column to form a third column kettle liquid (that is, light fraction-removal column kettle wastewater with a moisture content of greater than 99.9 wt %). In the POSM process, the aforementioned organic matters mainly include phenylethanol, acetophenone, ethylbenzene, styrene, small-molecule aldehydes, and small-molecule alcohols. In the POCHP process, the aforementioned organic matters mainly include dimethylbenzyl alcohol, isopropyl benzene, methyl styrene, small-molecule aldehydes, and small-molecule alcohols.

Preferably, the column kettle reboiler of the first rectifying column heats and reboils the material in the first rectifying column by using the third overhead material of the third rectifying column as a heat source, and cools the third overhead material preferably to 125° C. to 130° C. Preferably, the operating temperature of the first rectifying column is 100° C. to 150° C., for example, 110° C. to 130° C., the operating pressure is 0.1 MPa to 0.5 MPa, preferably 0.1 MPa to 0.2 MPa, and the concentration ratio is 1.2 to 2, preferably, 1.4 to 1.6. Preferably, the reflux ratio of the first rectifying column is 0.2 to 5, for example, 1 to 2.

In the present disclosure, the operating temperatures of each rectifying tower refer to column kettle temperatures. The operation of further limiting the operating temperatures helps to achieve process regulation in the operation of the present disclosure. The change of wastewater composition brings about by process fluctuations may lead to the changes in the column top temperature, so the column top temperature has no guiding significance, which is not limited in the present disclosure.

Preferably, the column kettle reboiler of the second rectifying column heats and reboils the material in the second rectifying column by using the first overhead material of the first rectifying column as a heat source, and cools the first overhead material preferably to 100° C. to 105° C. Preferably, the operating temperature of the second rectifying column is 60° C. to 90° C., for example, 70° C. to 80° C., the operating pressure is 20 kPa to 80 MPa, preferably 30 kPa to 50 kPa, and the concentration ratio is 1.5 to 5, preferably, 2 to 4. Preferably, the reflux ratio of the second rectifying column is 0.2 to 5, for example, 1 to 2. In the obtained second column kettle liquid, the COD is greater than $10^5$ mg/L, and the content of salts is 5 wt % to 40 wt %.

In the present disclosure, the concentration ratio refers to the flow ratio of the feed to the column kettle liquid of the corresponding rectifying column. For example, the concentration ratio of the first rectifying column refers to the flow ratio of the feed to the first column kettle material of the first rectifying column, that is, the flow ratio of the mixed wastewater to the first column kettle liquid; and the concentration ratio of the second rectifying column refers to the flow ratio of the feed to the second column kettle liquid of the second rectifying column, that is, the flow ratio of the first column kettle liquid to the second column kettle material.

In the first rectifying column and the second rectifying column, since the acid which may be present in the wastewater is mainly formic acid and acetic acid, and the boiling points of the formic acid and the acetic acid are between the boiling points of water and the main organic matters in the wastewater (such as phenylethyl alcohol, ethylbenzene, acetophenone, and the like), there may be enrichment of the acid in the middle-upper portion of the column, thereby causing corrosion to the equipment. In one embodiment, the alkaline solution (for example, a NaOH solution) is supplemented into the first rectifying column and the second rectifying column from upper portions thereof, respectively, to neutralize the acid that may be enriched in middle-upper portions of the columns, thereby preventing the acid from corroding the equipments. Preferably, the concentration of the NaOH solution supplemented into the first rectifying column and the second rectifying column is 20 wt % to 40 wt %, respectively, such as 24 wt %, 28 wt %, 32 wt %, and 36 wt %. The mass ratio of the solution to the wastewater is 0.001 to 0.01, preferably 0.002 to 0.004, such as 0.003. The wastewater is the to-be-treated production wastewater from the preparation of propylene oxide by co-oxidation. The supplementation of the alkaline solution can neutralize the acid that may be enriched in the middle-upper portions of the first rectifying column and the second rectifying column, thereby preventing the acid from corroding the equipments.

The column kettle reboiler of the third rectifying column heats and reboils the material in the third rectifying column by using steam as a heat source. Preferably, the operating temperature of the third rectifying column is 120° C. to 170° C., such as 130° C., 140° C., 150° C., and 160° C., the operating pressure is 0.1 MPa to 1 MPa, preferably 0.3 MPa to 0.5 MPa, and the reflux ratio is 10 to 50, preferably, 20 to 30. In the obtained third column kettle liquid, the COD is less than 2000 mg/L, and the B/C is greater than 0.3. The B/C is BOD/COD and refers to the biodegradability. The BOD refers to biochemical oxygen demand, is used for measuring the amount of oxygen required for the biodegradation of organic matters in water, and is the biodegradability index of water. The COD refers to chemical oxygen demand, is used for measuring the amount of oxygen consumed by organic matters in water by using potassium dichromate, and directly reflects the content of organic matters in water. The greater the value of B/C is, the better the biodegradability of water is. Preferably, the feed of the third rectifying column is pre-heated by a heat exchanger by using the third column kettle liquid as a heat source (preferably to 128° C. to 133° C.) to achieve a suitable feed temperature, which helps to achieve the separation of oil phase from water phase in a relatively short time. It is to be appreciated by those skilled in the art that the heat exchanger is provided on the feed line of the third rectifying column.

In the present disclosure, the heat exchanges between each stream of the first rectifying column, the second rectifying column and the third rectifying column of the multi-effect evaporation unit reduce the energy consumption for wastewater concentration and the amount of the second column kettle liquid, thereby reducing the material treatment amount in the subsequent incineration treatment and saving the construction cost and operation cost of the subsequent incineration unit.

In one embodiment, the treatment method further includes:

feeding the third overhead material to an oil-water separation device for oil-water separation to obtain an oil phase from the top thereof and an aqueous phase from the bottom thereof; and feeding the oil phase from the oil-water separation device to a recovery column for refining to remove a light fraction (for example, the light fraction having a boiling point of less than 120° C.) from the top of the recovery column, performing an incineration treatment, obtaining a recovery column kettle liquid from the recovery column kettle, and feeding the recovery column kettle liquid as a feed back to a refining unit in a system for preparing propylene oxide by co-oxidation for refining.

In this way, the reaction raw material converted from the peroxide in the first portion of wastewater can be extracted so that the reaction raw material is present in the recovery column kettle liquid and then fed back as the feed to the refining unit in the system for preparing propylene oxide by co-oxidation for refining. The material converted from the peroxide in the first portion of wastewater is refined by the refining unit in the system for preparing propylene oxide by co-oxidation and produced into by-products for sale or reuse as the raw material. Therefore, the capital consumption of the system for preparing propylene oxide by co-oxidation is reduced, and the production cost is reduced.

In one embodiment, the aqueous phase from the oil-water separation device may also be refluxed so that the aqueous phase from the oil-water separation device is subjected to oil-water separation again to separate the residual organic matters in the aqueous phase, thereby reducing the content of organic matters in the aqueous phase, and improving the quality of the oil phase obtained by the oil-water separation.

The operating temperature of the recovery column may be 80° C. to 150° C., preferably 90° C. to 110° C., the operating pressure is 20 kPa to 80 kPa, preferably 30 kPa to 50 kPa, and the reflux ratio is 0.2 to 5, preferably, 1 to 2.

The oil-water separation mainly refers to the remove of impurities or the separation of the oil phase from the water phase based on the difference in densities or chemical properties of water and oil using the principle of gravity settling or other physicochemical reactions. The recovery column is also a rectifying column, which separates different substances based on different boiling points of different substances in the mixture.

In the present disclosure, the incineration treatment in step (3) may be carried out in an incinerator. The salt residue obtained after the incineration treatment is mainly composed of sodium carbonate, and also contains metal elements. The metal elements are generally caused by the shedding of furnace bricks in the equipment used, and the type of the metal elements varies with the equipment used. In the present disclosure, the salt residue is mainly composed of sodium carbonate, and also contains the metal elements Al, Fe, Ni, Ti and Ca. The total content of metal elements Al, Fe, Ni, Ti and Ca is 10 mg/L to 500 mg/L.

In one embodiment, the treatment method further includes: feeding the salt residue to a salt residue treatment unit for treatment. The salt residue treatment unit includes a dissolving device and a filtering device.

The dissolving device is configured to dissolve the salt residue to obtain an alkaline salt residue solution with a pH of about 11, in which most of the metal elements Al, Fe, Ni, Ti and Ca precipitate out under the alkaline condition. Preferably, in the dissolving process, the mass of water for dissolving is 2 to 10 times, preferably 2 to 5 times, the mass of the salt residue, and the dissolving temperature is preferably 40° C. to 60° C. The content of suspended solids is less than or equal to 50 mg/L in the obtained salt residue solution. It is to be appreciated by those skilled in the art that the dissolving device may be a dissolving device commonly used in the art, such as a salt dissolving cell, a salt dissolving bucket and a salt dissolving tank.

The filtering device is configured to filter the salt residue solution to filter out precipitate therefrom to obtain a filtrate. The filtering device may be a filtering device commonly used in the art, such as a sintered filter, a ceramic membrane filter and a glass fiber filter. Preferably, the pore size of the filtering device is 0.1 μm to 10 μm, preferably 0.5 μm to 2 μm. The total content of Al, Fe, Ni, Ti and Ca in the filtrate obtained after filtering out the precipitation by the filtering device is less than 0.1 mg/L, which meets the seaward sewage discharge standard so that the filtrate can be discharged into the sea.

In the present disclosure, the COD of the aqueous phase obtained from the oil-water separation in the third rectifying column as the third column kettle liquid is less than 2000 mg/L, which meets the requirements of biochemical wastewater discharge index so that the aqueous phase may be subjected to biochemical treatment. For example, the soluble organic matters and part of insoluble organic matters in the wastewater may be removed under the decomposition of microorganism by artificial aeration and oxygen supply, which is a commonly used method for wastewater treatment in the art and will not be described in detail herein. In the present disclosure, after the biochemical treatment in step (4), the third column kettle liquid is subjected to the biochemical treatment to remove the organic matters in the third column kettle liquid which thus meets the discharge standard.

The present disclosure has the following beneficial effects.
(1) In the present disclosure, the peroxide in the first wastewater rapidly generates a large amount of active oxygen radicals [O] by means of the catalytic oxidation process and the catalytic oxidation reactor. In this way, the organic matters which are difficult to be biochemically decomposed in the first wastewater are catalytically decomposed into $CO_2$, $H_2O$, methanol, small-molecule carboxylic acid, and the like, and the peroxide in the first wastewater is completely converted into matters which can be produced into by-products or reused as raw materials after subjected to the treatment in the refining unit of the system for preparing propylene oxide by co-oxidation (for example, the peroxide ethylbenzene hydroperoxide (EBHP)/cumene hydrogen peroxide (CHP) are directionally converted into phenylethanol/dimethylbenzyl alcohol). Therefore, the concentration of the peroxide is reduced, the biodegradability of the wastewater is improved, and the difficulty and cost of the wastewater treatment are reduced. Moreover, the catalytic oxidation process can greatly reduce the amount of oxygen generated in the wastewater treatment process, thereby improving the process safety.
(2) Through the treatment method of the present disclosure, in the treatment in the multi-effect evaporation unit, the inter-stream heat exchanges between the first rectifying column, the second rectifying column and the third rectifying column can be achieved through column pressure matching so that the energy consumption of wastewater concentration is reduced and the amount of the second column kettle liquid is reduced, thereby reducing the material treatment amount in the subsequent incineration treatment and saving the construction cost and operation cost of the subsequent incineration unit. Meanwhile, the COD and the content of salts in the wastewater obtained after secondary concentration as the second column kettle liquid are greater than $10^5$ mg/L and 5 wt % to 40 wt %, respectively, and when the wastewater is fed to the incineration unit for incineration, no additional fuel is required, thereby reducing the cost of fuel.
(3) In the third column kettle liquid obtained after wastewater concentration and separation, the COD is less than 2000 mg/L, the B/C is greater than 0.3 so that the liquid can be directly conveyed to the biochemical unit for biochemical treatment, thereby reducing the cost of biochemical treatment.
(4) The third overhead material obtained after wastewater concentration and separation is subjected to oil-water separation to obtain an oil phase, and the obtained oil phase is refined by the recovery column and the light fractions are removed, so that the substance converted from the peroxide (for example, phenylethyl alcohol/dimethylbenzyl alcohol converted from the peroxide EBHP/CHP) can be extracted and is present in the recovery column kettle solution. The recovery column kettle solution is fed back to the refining unit in the system for preparing propylene oxide by co-oxidation for treatment to produce the styrene by-product/cumene by-product which can be produced for storage, use or sale. Therefore, the recovery utilization rate is high. The by-product of cumene can also be used as the raw material for the peroxidation unit of the system for preparing propylene oxide by the POCHP process. Therefore, the directional conversion of the peroxide can reduce the unit consumption of ethylbenzene/cumene, and thus the system for preparing propylene oxide by co-oxidation can save 8 to 13 million RMB a year.
(5) The salt residue obtained by incineration of the wastewater after secondary concentration as the second column kettle liquid by the incineration unit is sequentially dissolved and filtered to remove the metal elements Al, Fe, Ni, Ti and Ca. The total content of Al, Fe, Ni, Ti and Ca in the obtained filtrate is less than 0.1 mg/L and meets the seaward sewage discharge standard so that the filtrate can be discharged into the sea. Therefore, the salt residue obtained by incineration can be prevented from being treated as hazardous waste, thereby reducing the expense for treating the solid waste and reducing the treatment cost of solid waste.

As used herein, the word "optional" means "containing" or "not containing".

DETAILED DESCRIPTION

The technical solutions and effects thereof of the present disclosure will be further described hereinafter through the specific examples. The examples described below are intended to illustrate the present disclosure but are not be construed to limit the scope thereof. The simple modifications made to the present disclosure in according with the concept of the present disclosure are within the scope of the present disclosure.

In the following Examples and Comparative Examples, the sources of the main raw materials are as follows.
In the $MnO_2$/NiO complex catalyst,
$MnO_2$, analytically pure, available from Xiangtan Maien Industry and Trade Co., Ltd.;
NiO, analytical pure, available from Henan Sanwei Chemical Products Co., Ltd.; and
NaOH, industrial grade, available from Cangzhou Zhiming Chemical Products Production and Sales Co., Ltd.
Gas Phase Analysis Conditions:
The Agilent chromatographic determination was carried out online by using the Agilent HP-5 ms chromatographic column at a vaporization chamber temperature of 300° C. and a detector temperature of 300° C., and the temperature programming was also adopted: the temperature was held at 50° C. for 2 min, 100° C. for 1 min, and then raised to 300° C. at a rate of 10° C./min and held for 10 min.
Metal Element Analysis Conditions:
The sample was pre-treated by microwave digestion. The temperature of the sample was raised at 800 W for 10 min and held for 5 min, raised at 1200 W for 5 min and held for 20 min, and then cooled for 5 min. The content of the metal element was analyzed by inductively coupled plasma atomic emission spectrometry at a power of 1.2 kW, an atomizer flow rate of 15 L/min, an observation height of 8 mm, an injection rinse duration of 30 s, a detection wavelength of 204 nm, and a pump speed of 7 rad/min.

Example 1

Figure 1:
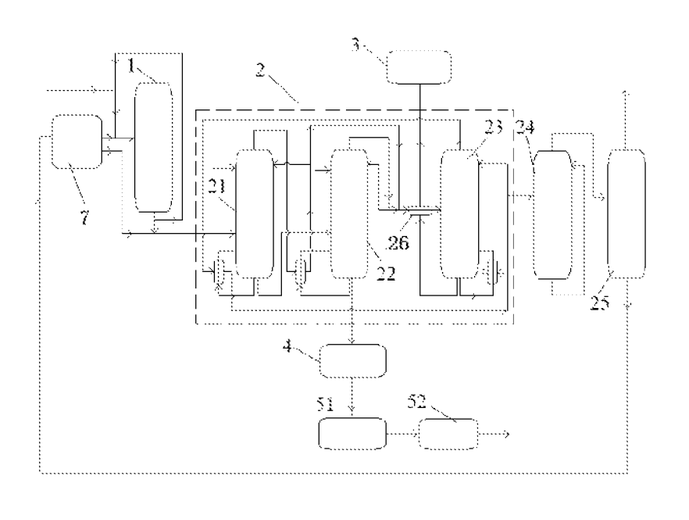
FIG. 1 is a process flowchart of a method for treating production wastewater from the preparation of propylene oxide by co-oxidation according to example 1 of the present disclosure.

As shown in FIG. 1, a method for treating production wastewater from the preparation of propylene oxide by co-oxidation is as follows:

(1) A first portion of wastewater was pre-fed to a catalytic oxidation reactor 1 for a catalytic oxidation reaction to remove peroxides therein and obtain effluent wastewater from the outlet of the catalytic oxidation reactor 1. A portion of the effluent wastewater from the catalytic oxidation reactor 1 was cycled from the inlet of the catalytic oxidation reactor 1 to the catalytic oxidation reactor 1. An alkaline solution was added to the cycled portion of the effluent wastewater so that the alkaline solution was conveyed into the catalytic oxidation reactor 1 along with the cycled portion of the effluent wastewater to increase the pH of the material system in the catalytic oxidation reactor 1.

(2) The mixed wastewater obtained by mixing the effluent wastewater and a second portion of wastewater was fed into a first rectifying tower 21 in a multi-effect evaporation unit 2 to be subjected to a rectifying treatment for concentration so as to obtain a first overhead material from the top of the column and a first concentrated wastewater from the bottom of the column as a first column kettle liquid. An alkaline solution was fed from an upper portion of the first rectifying column 21 into the first rectifying column 21.

The first column kettle liquid was then fed to a second rectifying column 22 for rectification to be further concentrated to obtain a second overhead material from the top of the column and secondary concentrated wastewater from the kettle as a second column kettle liquid. An alkaline solution was fed from an upper portion of the second rectifying column 22 into the second rectifying column 22.

The first overhead material and the second overhead material were then fed into a third rectifying column 23 for rectification to separate oil and water, to obtain an oil phase as a third overhead material from the top of the column and an aqueous phase as a third column kettle liquid from the bottom of the column.

The first column kettle reboiler heated and reboiled the material in the first rectifying column with the third overhead material as a heat source and cooled the third overhead material. The second column kettle reboiler heated and reboiled the material in the second rectifying column with the first overhead material as a heat source and cooled the first overhead material. The third column kettle reboiler heated and reboiled the material in the third rectifying column with steam as a heat source.

A heat exchanger 26 pre-heated the feed to the third rectifying column 23 with the third column kettle liquid as a heat source.

The third overhead material was fed into an oil-water separation device 24 for oil-water separation to obtain an oil phase and an aqueous phase from the top and the bottom of the oil-water separation device, respectively. The aqueous phase from the oil-water separation device 24 was refluxed.

The oil phase from the oil-water separation device 24 was fed to a recovery column 25 for refining to remove light components having a boiling point of less than 150° C. from the top of the recovery column and a recovery column kettle liquid was obtained from the column.

The recovery column kettle liquid from the recovery column 25 was fed back to the refining unit in a system 7 for preparing propylene oxide by co-oxidation.

(3) The second column kettle liquid was fed to an incineration unit 4 for incineration to obtain salt residue. The salt residue was successively subjected to the dissolving treatment and the filtering treatment to remove the metal elements Al, Fe, Ni, Ti and Ca to obtain a filtrate. The dissolving treatment was to feed the salt residue from the incineration unit 4 to a dissolving device 51 for dissolving to obtain an alkaline salt residue solution in which the metal elements Al, Fe, Ni, Ti and Ca precipitated out in an alkaline environment. The filtration treatment was to feed the salt residue solution from the dissolving device 51 to a filtrating device 52 to filter out the precipitate therein to obtain a filtrate.

(4) The third column kettle liquid was fed to a biochemical unit 3 for biochemical treatment to remove the organic matters therein.

The first portion of wastewater referred to the wastewater with a peroxide content of more than 2000 mg/L in the production wastewater from the preparation of propylene oxide by co-oxidation, and the second portion of wastewater referred to the wastewater with a peroxide content of less than 50 mg/L in the production wastewater from the preparation of propylene oxide by co-oxidation.

The Treatment Conditions are as Follows:

The system 7 for preparing propylene oxide by co-oxidation was a POSM system from Yantai Wanhua Industrial Park. In the production wastewater, the peroxide content was 25000 mg/L and the COD was 80000 mg/L in the first portion of wastewater, and the peroxide content was 40 mg/L in the second portion of wastewater.

The catalyst used for the catalytic oxidation reaction was a $MnO_2/NiO$ complex catalyst, where the mass ratio of $MnO_2$ to NiO was 0.5:1. The temperature of the catalytic oxidation reaction was 70° C., and the feed space velocity was 2 $h^{-1}$. The cycling ratio of the effluent wastewater obtained after decomposition of the catalytic oxidation reaction was 2. The alkaline solution fed into the cycled portion of the effluent wastewater was a NaOH solution with a concentration of 32 wt %, and the addition amount of the alkaline solution was an amount which can make the pH of the material system in the catalytic oxidation reactor 1 rise to 9.

In the mixed wastewater obtained by mixing the effluent wastewater with the second portion of wastewater, the COD was 30000 mg/L, the pH was 10, and the content of salts was 5 wt %.

The operating temperature of the first rectifying column 21 was 110° C., the operating pressure was 0.1 MPa, the concentration ratio was 1.4, and the reflux ratio was 2. The alkaline solution added from the upper portion of the first rectifying column 21 was a NaOH solution with a concentration of 32 wt %, and the mass ratio of the NaOH solution to the wastewater was 0.002.

The operating temperature of the second rectifying column 22 was 80° C., the operating pressure was 30 kPa, the reflux ratio was 2, and the concentration rate was 2. The alkaline solution added from the upper portion of the second rectifying column 22 was a NaOH solution with a concentration of 32 wt %, and the mass ratio of the NaOH solution to the wastewater was 0.002. The mass of the water for dissolving was 4 times the mass of the salt residue, and the dissolving temperature was 50° C. When the salt residue was filtered, the filtering device used was a sintered filter having a pore size of 2 μm.

The operating temperature of the third rectifying column 23 was 150° C., the operating pressure was 0.5 MPa, and the reflux ratio was 20. The operating temperature of the recovery column 25 was 90° C., the operating pressure was 50 kPa, and the reflux ratio was 2.

The Treatment Results are as Follows:

The pH of the effluent wastewater obtained after decomposition of the catalytic oxidation reaction was 10, and the peroxide content was 100 mg/L. The recovery rate of EBHP directionally converted into phenylethyl alcohol was 83%.

In the second column kettle liquid as the secondary concentrated wastewater, the COD was $1.2 \times 10^5$ mg/L, and the content of salts was 20 wt %.

The total content of the metal elements Al, Fe, Ni, Ti and Ca in the salt residue obtained by incineration of the second column kettle liquid through the incineration system 4 was 50 mg/L.

In the obtained salt residue solution, the content of suspended solids was 20 mg/L.

The total content of the metal elements Al, Fe, Ni, Ti and Ca in the filtrate obtained after the filtration treatment was 0.09 mg/L.

In the third column kettle liquid, the COD was 1900 mg/L, and the B/C was 0.33, which meets the requirement of biochemical wastewater discharge index, and after the biochemical treatment, the COD was less than 50 mg/L.

Example 2

The treatment method in Example 2 is the same as that in Example 1.

The Treatment Conditions are as Follows:

The system 7 for preparing propylene oxide by co-oxidation was a POSM system from Yantai Wanhua Industrial Park. In the production wastewater, the peroxide content was 28000 mg/L and the COD was 100000 mg/L in the first portion of wastewater, and the peroxide content was 45 mg/L in the second portion of wastewater.

The catalyst used for the catalytic oxidation reaction was a $MnO_2/NiO$ complex catalyst, where the mass ratio of $MnO_2$ to NiO was 2:1. The temperature of the catalytic oxidation reaction was 70° C., and the feed space velocity was 2 $h^{-1}$. The cycling ratio of the effluent wastewater obtained after decomposition of the catalytic oxidation reaction was 1.5. The alkaline solution fed into the cycled portion of the effluent wastewater was a NaOH solution with a concentration of 25 wt %, and the addition amount of the alkaline solution was an amount which can make the pH of the material system in the catalytic oxidation reactor 1 rise to 10.

In the mixed wastewater obtained by mixing the effluent wastewater with the second portion of wastewater, the COD was 50000 mg/L, the pH was 8, and the content of salts was 8 wt %.

The operating temperature of the first rectifying column 21 was 130° C., the operating pressure was 0.2 MPa, the concentration ratio was 1.5, and the reflux ratio was 5. The alkaline solution added from the upper portion of the first rectifying column 21 was a NaOH solution with a concentration of 25 wt %, and the mass ratio of the NaOH solution to the wastewater was 0.004.

The operating temperature of the second rectifying column 22 was 90° C., the operating pressure was 20 kPa, the concentration rate was 5, and the reflux ratio was 1. The alkaline solution added from the upper portion of the second rectifying column 22 was a NaOH solution with a concentration of 25 wt %, and the mass ratio of the NaOH solution to the wastewater was 0.004. The mass of the water for dissolving was 10 times the mass of the salt residue, and the dissolving temperature was 50° C. When the salt residue was filtered, the filtering device used was a ceramic membrane filter having a pore size of 0.5 μm.

The operating temperature of the third rectifying column 23 was 170° C., the operating pressure was 1 MPa, and the reflux ratio was 20. The operating temperature of the recovery column 25 was 150° C., the operating pressure was 80 kPa, and the reflux ratio was 1.

The Treatment Results are as Follows:

The pH of the effluent wastewater obtained after decomposition of the catalytic oxidation reaction was 9, and the peroxide content was 1000 mg/L. The recovery rate of EBHP directionally converted into phenylethyl alcohol was 81%.

In the second column kettle liquid as the secondary concentrated wastewater, the COD was $10^6$ mg/L, and the content of salts was 40 wt %.

The total content of the metal elements Al, Fe, Ni, Ti and Ca in the salt residue obtained by incineration of the second column kettle liquid through the incineration system 4 was 500 mg/L.

In the obtained salt residue solution, the content of suspended solids was 50 mg/L.

The total content of the metal elements Al, Fe, Ni, Ti and Ca in the filtrate obtained after the filtration treatment was 0.09 mg/L.

In the third column kettle liquid, the COD was 500 mg/L, and the B/C was 0.4, which meets the requirement of biochemical wastewater discharge index, and after the biochemical treatment, the COD was less than 50 mg/L.

Example 3

The treatment method in Example 3 is the same as that in Example 1.

The Treatment Conditions are as Follows:

The system 7 for preparing propylene oxide by co-oxidation was a POSM system from Yantai Wanhua Industrial Park. In the production wastewater, the peroxide content was 20000 mg/L and the COD was 10000 mg/L in the first portion of wastewater, and the peroxide content was 30 mg/L in the second portion of wastewater.

The catalyst used for the catalytic oxidation reaction was a $MnO_2/NiO$ complex catalyst, where the mass ratio of $MnO_2$ to NiO was 1:1. The temperature of the catalytic oxidation reaction was 20° C., and the feed space velocity was 4 $h^{-1}$. The cycling ratio of the effluent wastewater obtained after decomposition by the catalytic oxidation reaction was 1.5. The alkaline solution fed into the cycled portion of the effluent wastewater was a NaOH solution with a concentration of 20 wt %, and the addition amount of the alkaline solution was an amount which can make the pH of the material system in the catalytic oxidation reactor 1 rise to 8.

In the mixed wastewater obtained by mixing the effluent wastewater with the second portion of wastewater, the COD was 10000 mg/L, the pH was 12, and the content of salts was 1 wt %.

The operating temperature of the first rectifying column 21 was 150° C., the operating pressure was 0.5 MPa, the concentration ratio was 1.6, and the reflux ratio was 1.5. The alkaline solution added from the upper portion of the first rectifying column 21 was a NaOH solution with a concentration of 20 wt %, and the mass ratio of the NaOH solution to the wastewater was 0.001.

The operating temperature of the second rectifying column 22 was 75° C., the operating pressure was 40 kPa, the concentration rate was 3, and the reflux ratio was 5. The alkaline solution added from the upper portion of the second rectifying column 22 was a NaOH solution with a concentration of 20 wt %, and the mass ratio of the NaOH solution to the wastewater was 0.001.

The mass of the water for dissolving was 4.5 times the mass of the salt residue, and the dissolving temperature was 50° C. When the salt residue was filtered, the filtering device used was a glass fiber filter having a pore size of 1 μm.

The operating temperature of the third rectifying column 23 was 140° C., the operating pressure was 0.4 MPa, and the reflux ratio was 10. The operating temperature of the recovery column 25 was 110° C., the operating pressure was 40 kPa, and the reflux ratio was 1.5.

The treatment results are as follows:

The pH of the effluent wastewater obtained after decomposition through the catalytic oxidation reaction was 13, and the peroxide content was 200 mg/L. The recovery rate of EBHP directionally converted into phenylethyl alcohol was 85%.

In the second column kettle liquid as the secondary concentrated wastewater, the COD was 300000 mg/L, and the content of salts was 5 wt %.

The total content of the metal elements Al, Fe, Ni, Ti and Ca in the salt residue obtained by incineration of the second column kettle liquid through the incineration system 4 was 100 mg/L.

In the obtained salt residue solution, the content of suspended solids was 10 mg/L.

The total content of the metal elements Al, Fe, Ni, Ti and Ca in the filtrate obtained after the filtration treatment was 0.05 mg/L.

In the third column kettle liquid, the COD was 1500 mg/L, and the B/C was 0.4, which meets the requirement of biochemical wastewater discharge index, and after the biochemical treatment, the COD was less than 50 mg/L.

Example 4

The treatment method in Example 4 is the same as that in Example 1.
The Treatment Conditions are as Follows:

The system 7 for preparing propylene oxide by co-oxidation was a POSM system from Yantai Wanhua Industrial Park. In the production wastewater, the peroxide content was 10000 mg/L and the COD was 40000 mg/L in the first portion of wastewater, and the peroxide content was 30 mg/L in the second portion of wastewater.

The catalyst used for the catalytic oxidation reaction was a MnO$_2$/NiO complex catalyst, where the mass ratio of MnO$_2$ to NiO was 1.5:1. The temperature of the catalytic oxidation reaction was 50° C., and the feed space velocity was 0.5 h$^{-1}$. The cycling ratio of the effluent wastewater obtained after decomposition by the catalytic oxidation reaction was 1. The alkaline solution fed into the cycled portion of the effluent wastewater was a NaOH solution with a concentration of 15 wt %, and the addition amount of the alkaline solution was an amount which can make the pH of the material system in the catalytic oxidation reactor 1 rise to 8.

In the mixed wastewater obtained by mixing the effluent wastewater with the second portion of wastewater, the COD was 20000 mg/L, the pH was 5, and the content of salts was 20 wt %.

The operating temperature of the first rectifying column 21 was 120° C., the operating pressure was 0.15 MPa, the concentration ratio was 1.5, and the reflux ratio was 0.2. The alkaline solution added from the upper portion of the first rectifying column 21 was a NaOH solution with a concentration of 15 wt %, and the mass ratio of the NaOH solution to the wastewater was 0.01.

The operating temperature of the second rectifying column 22 was 60° C., the operating pressure was 80 kPa, the concentration rate was 2, and the reflux ratio was 0.2. The alkaline solution added from the upper portion of the second rectifying column 22 was a NaOH solution with a concentration of 15 wt %, and the mass ratio of the NaOH solution to the wastewater was 0.01. The mass of the water for dissolving was 5 times the mass of the salt residue, and the dissolving temperature was 50° C. When the salt residue was filtered, the filtering device used was a sintered filter having a pore size of 0.1 μm.

The operating temperature of the third rectifying column 23 was 120° C., the operating pressure was 0.1 MPa, and the reflux ratio was 50. The operating temperature of the recovery column 25 was 80° C., the operating pressure was 20 kPa, and the reflux ratio was 0.2.

The Treatment Results are as Follows:

The pH of the effluent wastewater obtained after decomposition through the catalytic oxidation reaction was 6, and the peroxide content was 300 mg/L. The recovery rate of EBHP directionally converted into phenylethyl alcohol was 92%.

In the second column kettle liquid as the secondary concentrated wastewater, the COD was 200000 mg/L, and the content of salts was 30 wt %.

The total content of the metal elements Al, Fe, Ni, Ti and Ca in the salt residue obtained by incineration of the second column kettle liquid through the incineration system 4 was 200 mg/L.

In the obtained salt residue solution, the content of suspended solids was 10 mg/L.

The total content of the metal elements Al, Fe, Ni, Ti and Ca in the filtrate obtained after the filtration treatment was 0.06 mg/L.

In the third column kettle liquid, the COD was 1500 mg/L, and the B/C was 0.5, which meets the requirement of biochemical wastewater discharge index, and after the biochemical treatment, the COD was less than 50 mg/L.

Example 5

The treatment method in Example 5 is the same as that in Example 1.
The Treatment Conditions are as Follows:

The system 7 for preparing propylene oxide by co-oxidation was a POCHP system from Yantai Wanhua Industrial Park. In the production wastewater, the peroxide content was 3000 mg/L and the COD was 20000 mg/L in the first portion of wastewater, and the peroxide content was 30 mg/L in the second portion of wastewater.

The catalyst used for the catalytic oxidation reaction was a MnO$_2$/NiO complex catalyst, where the mass ratio of MnO$_2$ to NiO was 1.2:1. The temperature of the catalytic oxidation reaction was 60° C., and the feed space velocity was 1.5 h$^{-1}$. The cycling ratio of the effluent wastewater obtained after decomposition by the catalytic oxidation reaction was 5. The alkaline solution fed into the cycled portion of the effluent wastewater was a NaOH solution with a concentration of 10 wt %, and the addition amount of the alkaline solution was an amount which can make the pH of the material system in the catalytic oxidation reactor 1 rise to 9.5.

In the mixed wastewater obtained by mixing the effluent wastewater with the second portion of wastewater, the COD was 50000 mg/L, the pH was 9, and the content of salts was 10 wt %.

The operating temperature of the first rectifying column 21 was 100° C., the operating pressure was 0.12 MPa, the concentration ratio was 1.2, and the reflux ratio was 2. The alkaline solution added from the upper portion of the first rectifying column 21 was a NaOH solution with a concentration of 10 wt %, and the mass ratio of the NaOH solution to the wastewater was 0.003.

The operating temperature of the second rectifying column 22 was 70° C., the operating pressure was 50 kPa, the reflux ratio was 1.5, and the concentration rate was 4. The alkaline solution added from the upper portion of the second rectifying column 22 was a NaOH solution with a concentration of 10 wt %, and the mass ratio of the NaOH solution to the wastewater was 0.03. The mass of the water for dissolving was 4 times the mass of the salt residue, and the dissolving temperature was 50° C. When the salt residue was filtered, the filtering device used was a ceramic membrane filter having a pore size of 10 μm.

The operating temperature of the third rectifying column 23 was 130° C., the operating pressure was 0.3 MPa, and the reflux ratio was 30. The operating temperature of the recovery column 25 was 100° C., the operating pressure was 30 kPa, and the reflux ratio was 5.

The Treatment Results are as Follows:

The pH of the effluent wastewater obtained after decomposition through the catalytic oxidation reaction was 9.5, and the peroxide content was 50 mg/L. The recovery rate of EBHP directionally converted into phenylethyl alcohol was 94%.

In the second column kettle liquid as the secondary concentrated wastewater, the COD was 300000 mg/L, and the content of salts was 25 wt %.

The total content of the metal elements Al, Fe, Ni, Ti and Ca in the salt residue obtained by incineration of the second column kettle liquid through the incineration system 4 was 10 mg/L.

In the obtained salt residue solution, the content of suspended solids was 8 mg/L.

The total content of the metal elements Al, Fe, Ni, Ti and Ca in the filtrate obtained after the filtration treatment was 0.08 mg/L.

In the third column kettle liquid, the COD was 1800 mg/L, and the B/C was 0.35, which meets the requirement of biochemical wastewater discharge index, and after the biochemical treatment, the COD was less than 50 mg/L.

What is claimed is:

1. A method for treating production wastewater from preparation of propylene oxide by co-oxidation, wherein the production wastewater comprises a first portion of wastewater having a peroxide content of 2000 mg/L or more and a second portion of wastewater having a peroxide content of 50 mg/L or less, and the method comprises the following steps:
   (1) pre-subjecting the first portion of wastewater to a catalytic oxidation treatment to remove peroxides therefrom to obtain effluent wastewater;
   (2) feeding mixed wastewater obtained by mixing the effluent wastewater with the second portion of wastewater into a multi-effect evaporation unit for treatment, wherein the multi-effect evaporation unit comprises:
      a first rectifying column, configured to rectify the mixed wastewater to concentrate the mixed wastewater to obtain a first overhead material from a top of the first rectifying column and first concentrated wastewater from a bottom of the first rectifying column as a first column kettle liquid;
      a second rectifying column, configured to rectify the first column kettle liquid from the first rectifying column to further concentrate the first column kettle liquid to obtain a second overhead material from a top of the second rectifying column and second concentrated wastewater from a bottom of the second rectifying column as a second column kettle liquid; and
      a third rectifying column, configured to rectify the first overhead material from the first rectifying column and the second overhead material from the second rectifying column for oil-water separation to obtain an oil phase from a top of the third rectifying column as a third overhead material and an aqueous phase from a bottom of the third rectifying column as a third column kettle liquid;
   (3) subjecting the second column kettle liquid to an incineration treatment to obtain a salt residue; and
   (4) subjecting the third column kettle liquid to a biochemical treatment to remove organic matters therefrom.

2. The treatment method according to claim 1, further comprising the following steps:
   feeding the third overhead material to an oil-water separation device for oil-water separation to obtain an oil phase from a top thereof and an aqueous phase from a bottom thereof; and
   feeding the oil phase from the oil-water separation device to a recovery column for refining to remove a light fraction having a boiling point of less than 150° C. from a top of the recovery column and obtain a recovery column kettle liquid from a recovery column kettle, and feeding the recovery column kettle liquid as a feed back to a refining unit in a system for preparing propylene oxide by co-oxidation for refining.

3. The treatment method according to claim 1, further comprising: feeding the salt residue to a salt residue treatment unit for sequentially dissolving and filtering, wherein the salt residue treatment unit comprises:
   a dissolving device, configured to dissolve the salt residue to obtain an alkaline salt residue solution; and
   a filtering device, configured to filter the salt residue solution to filter out precipitate therefrom to obtain a filtrate.

4. The treatment method according to claim 1, wherein the catalytic oxidation treatment is carried out in a catalytic oxidation reactor, and wherein the treatment method further comprises cycling a portion of the effluent wastewater to an inlet of the catalytic oxidation reactor in a cycling ratio of 1 to 5.

5. The treatment method according to claim 4, wherein the treatment method further comprises: adding an alkaline solution to the cycled portion of the effluent wastewater to increase a pH of a material system in the catalytic oxidation reactor.

6. The treatment method according to claim 1, further comprising:
   supplementing an alkaline solution into the first rectifying column and the second rectifying column from upper portions thereof, respectively, to neutralize the acid enriched in middle-upper portions of the columns.

7. The treatment method according to claim 5, wherein the alkaline solution is a NaOH solution with a concentration of 20 wt % to 40 wt %.

8. The treatment method according to claim 1, wherein a catalyst used for the catalytic oxidation treatment is a complex catalyst of $MnO_2$ and NiO, wherein the mass ratio of $MnO_2$ to NiO is (0.5 to 2):1.

9. The treatment method according to claim 1, wherein the catalytic oxidation treatment is carried out under the following catalytic oxidation conditions: a temperature of 20° C. to 80° C. and a feed space velocity of 0.5 $h^{-1}$ to 4 $h^{-1}$.

10. The treatment method according to claim 1, wherein
an operating temperature of the first rectifying column is 100° C. to 150° C., an operating pressure is 0.1 MPa to 0.5 MPa, and a concentration ratio is 1.2 to 2;
an operating temperature of the second rectifying column is 60° C. to 90° C., an operating pressure is 20 kPa to 80 kPa, and a concentration ratio is 1.5 to 5; and
an operating temperature of the third rectifying column is 120° C. to 170° C., an operating pressure is 0.1 MPa to 1 MPa, and a reflux ratio is 10 to 50.

11. The treatment method according to claim 1, wherein in step (2), a column kettle reboiler of the first rectifying column heats and reboils the material inside the first rectifying column by using the third overhead material of the third rectifying column as a heat source, and cools the third overhead material; and
a column kettle reboiler of the second rectifying column heats and reboils the material in the second rectifying column by using the first overhead material of the first rectifying column as a heat source, and cools the first overhead material.

* * * * *